United States Patent
Yanagisawa

(10) Patent No.: US 7,695,793 B2
(45) Date of Patent: Apr. 13, 2010

(54) COMPOUND, OPTICAL FILTER AND OPTICAL RECORDING MATERIAL USING THE SAME

(75) Inventor: Satoshi Yanagisawa, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 12/299,052

(22) PCT Filed: Mar. 5, 2007

(86) PCT No.: PCT/JP2007/054190

§ 371 (c)(1),
(2), (4) Date: Oct. 30, 2008

(87) PCT Pub. No.: WO2007/129503

PCT Pub. Date: Nov. 15, 2007

(65) Prior Publication Data
US 2009/0137800 A1    May 28, 2009

(30) Foreign Application Priority Data
May 8, 2006  (JP) ............... 2006-129404
Feb. 22, 2007 (JP) ............... 2007-042375

(51) Int. Cl.
B32B 3/02    (2006.01)
G11B 7/247   (2006.01)
C07C 251/00  (2006.01)
C07D 209/14  (2006.01)

(52) U.S. Cl. ............ 428/64.8; 430/270.18; 548/455; 564/248

(58) Field of Classification Search ............ 428/64.4, 428/64.8; 564/248; 548/455; 430/270.18
See application file for complete search history.

(56) References Cited

U.S. PATENT DOCUMENTS

| 4,886,835 | A | * | 12/1989 | Malleron et al. | 514/532 |
| 4,897,494 | A | * | 1/1990 | Psaar et al. | 548/455 |
| 4,996,328 | A | * | 2/1991 | Mathiaparanam | 548/427 |
| 7,074,938 | B2 | * | 7/2006 | Jacobs et al. | 548/455 |

FOREIGN PATENT DOCUMENTS

| CS | 221362 B1 * | 4/1983 |
| JP | 2001-301333 | 10/2001 |
| JP | 2003-57436 | 2/2003 |
| JP | 2004-45887 | 2/2004 |
| JP | 2004-174838 | 6/2004 |
| JP | 2005-59601 | 3/2005 |

OTHER PUBLICATIONS

Reidl, S. et al., "Polymethine dyes. IX. Polymethine dyes of diphenyl- and 2,2'-dinapthylamine," Chemische Berichte, 1962, 95, 228-232.*
Nyerges, M. et al., "The generation and reactivity of N-substituted, stabilized alpha,beta:gamma,delta-unsaturated ylides," Tetrahedron, 2002, 58, 989-995.*
Clough, S. et al., "Reactions of (Z)-3-aryl-3-chloropropenals with nucleophiles: stereoselective formation of (E)-vinylogous esters, (E)-vinylogous amides, and vinamidinium salts," Tetrahedron, 2005, 61, 7554-7561.*
STN search for dual phenyl/naphthyl or dual heterocyclic substituents performed on Jun. 28, 2009. Imported as STN3.pdf.*
STN search for a phenyl/naphthyl with a heterocyclic ring performed on Jun. 28, 2009. Imported as STN4.pdf.*
STN search history updated and refined. Performed on Jan. 12, 2010.*
DD 122525 A1 (Fischer, G.W.), Oct. 12, 1976, Claims; pp. 11 to 13 (Family: none).
Fischer, G.W., Vinylogous acyl compounds, XIV. Reaction of vinylogous acid chlorides and Vilsmeier reagents with 4-(4-nitrobenzyl) pyridine, Journal fuer Praktische Chemie, 1975, vol. 317, No. 5, p. 779-790, (particularly, formula 11).

* cited by examiner

*Primary Examiner*—Mark Ruthkosky
*Assistant Examiner*—Gerard T Higgins
(74) *Attorney, Agent, or Firm*—Young & Thompson

(57) ABSTRACT

A compound represented by the following general formula (I),

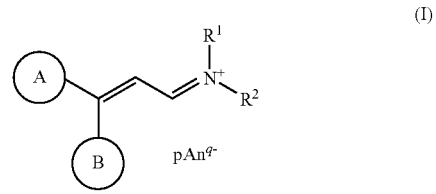

wherein ring A and ring B each independently represent a benzene, naphthalene, or heterocyclic ring which may be substituted; $R^1$ and $R^2$ each independently represent an alkyl group having 1 to 8 carbon atoms which may be substituted; $R^1$ and $R^2$ may be linked together to form a ring; a methylene group of the alkyl group having 1 to 8 carbon atoms may be replaced by —O— or —CH=CH—; $An^{q-}$ represents a q-valent anion, where q is 1 or 2; p represents a coefficient to keep the charge neutral.

14 Claims, No Drawings

COMPOUND, OPTICAL FILTER AND OPTICAL RECORDING MATERIAL USING THE SAME

TECHNICAL FIELD

The present invention relates to a novel compound derived from biarylethylene, and an optical filter and an optical recording material, both using the compound. The compound is useful as an optical element and the like, especially as a light absorber included in an optical filter for an image display unit and as an optical recording agent included in an optical recording material used for an optical recording layer of an optical recording medium, which is recorded and reproduced by laser light.

BACKGROUND ART

Compounds having strong absorptions in a range of from 450 nm to 1,100 nm, especially those having maximum absorptions (λmax) between 480 and 620 nm are used as optical elements for the optical recording layers of optical recording media such as DVD±R and the like, and for optical filters for the image display units such as liquid crystal displays (LCD), plasma display panels (PDP), electroluminescence displays (ELD), cathode ray tube displays (CRT), fluorescent displays, field emission displays, and the like.

For example, one application of the optical element in the image display unit is a light absorber for the color filter. The image display unit displays color images by a combination of three primary colors, namely, red, blue, and green. However, light which displays color images contains light between green and red, for example, between 550 and 600 nm, which causes lowering of the display quality. Also, light between 750 and 1,100 nm is contained, which may cause a malfunction of an infrared remote control. Thus, there is used an optical filter containing a light absorbing compound (a light absorber) which selectively absorbs light of these unnecessary wavelengths.

Further, the optical filter is also desired to have a function of preventing reflection or glare of outside light such as fluorescent lamps and the like. In order to prevent reflection or glare, the optical filter needs to absorb light of wavelength between 480 and 500 nm, in addition to its function to selectively absorb the above-mentioned light of unnecessary wavelengths. The light in this region is close to the bright line needed to display images. Thus, in order not to affect the image quality, the light absorption curve by the light absorber is required to be especially steep, namely the half bandwidth at λmax is required to be small.

Furthermore, the light absorber is also required not to lose its function by light, heat, and the like.

As an optical filter comprising the light absorber, for example, the following Patent Document 1 discloses an optical filter which uses a dipyrromethene metal chelate compound having a maximum absorption wavelength between 440 and 510 nm, and Patent Document 2 discloses an optical filter which utilizes a porphyrin compound having a maximum absorption wavelength between 440 and 510 nm. However, the compounds used for these optical filters do not provide satisfactory performances in terms of absorption wavelength characteristics or compatibility with the solvents and binder resins. Thus, these optical filters did not show satisfactory performances between 480 and 500 nm.

Further, in the above-mentioned optical recording media, the wavelength of a semiconductor laser used for recording and reproduction is between 750 and 830 nm for CD-R and between 620 and 690 nm for DVD±R. However, in order to realize further increase in the recording capacity, an optical disc which uses short-wavelength laser light, for example, one which uses recording light of 380 to 420 nm in wavelength is under study.

In an optical recording medium for the short-wavelength recording light, various compounds are used to form the optical recording layer. For example, there are reported in Patent Document 3 an cyanine-based dye, in Patent Document 4 a metal complex of triazole compounds, and in Patent Document 5 a porphyrin compound. However, these compounds were not necessarily adequate as an optical recording material used for formation of an optical recording layer, in terms of absorption wavelength characteristics and light resistance.

Patent Document No. 1: Japanese Patent Laid-Open Publication No. 2003-57436

Patent Document No. 2: Japanese Patent Laid-Open Publication No. 2004-45887

Patent Document No. 3: Japanese Patent Laid-Open Publication No. 2001-301333

Patent Document No. 4: Japanese Patent Laid-Open Publication No. 2004-174838

Patent Document No. 5: Japanese Patent Laid-Open Publication No. 2005-59601

DISCLOSURE OF THE INVENTION

Problems to be Solved by the Invention

Accordingly, an object of the present invention is to provide a compound which has excellent absorption wavelength characteristics and light resistance, and is suitable for optical elements used especially in an optical filter for an image display unit and in an optical recording material recorded and reproduced by laser light.

MEANS FOR SOLVING THE PROBLEMS

The present inventors conducted diligent research and, as a result, found that a compound with a specific structure derived from biarylethylene has excellent absorption wavelength characteristics and light resistance. The inventors envisaged that the use of this compound may solve the above-mentioned problems.

The present invention has been made based on the above findings and accomplished the above-mentioned object by providing a compound represented by the following general formula (I):

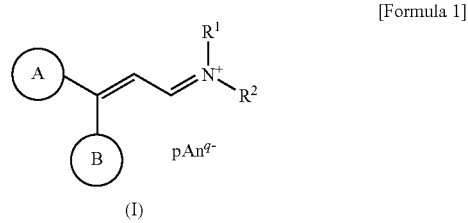

[Formula 1]

(I)

wherein ring A and ring B each independently represent a benzene, naphthalene, or heterocyclic ring which may be substituted; $R^1$ and $R^2$ each independently represent an alkyl group having 1 to 8 carbon atoms which may be substituted; $R^1$ and $R^2$ may be linked together to form a ring; a methylene group of the alkyl group having 1 to 8 carbon atoms may be replaced by —O— or —CH=CH—; $An^{q-}$ represents a q-valent anion, where q is 1 or 2; p represents a coefficient to keep the charge neutral.

Further, the present invention has accomplished the object by providing a compound represented by the following general formula (II):

[Formula 2]

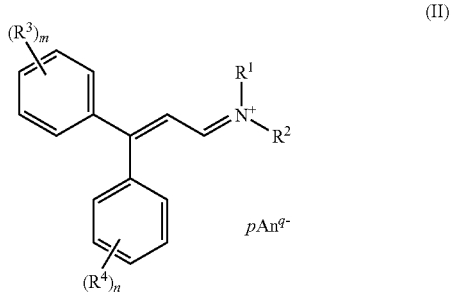

(II)

wherein $R^1$, $R^2$, $An^{q-}$, q, and p are the same as in the general formula (I); $R^3$ and $R^4$ each independently represent a hydrogen atom, an alkyl group having 1 to 8 carbon atoms which may be substituted, an aryl group having 6 to 20 carbon atoms which may be substituted, an arylalkyl group having 7 to 20 carbon atoms which may be substituted, a nitro group, an amino group, a halogen atom, a cyano group, or a heterocyclic group having 2 to 20 carbon atoms; m and n are each independently an integer from 1 to 5; a methylene group of the alkyl group having 1 to 8 carbon atoms may be replaced by —O— or —CH=CH—.

Also, the present invention has accomplished the object by providing a compound represented by the following general formula (III).

[Formula 3]

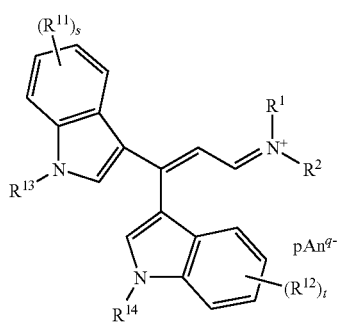

(III)

wherein $R^1$, $R^2$, $An^{q-}$, q, and p are the same as in the general formula (I); $R^{11}$ and $R^{12}$ each independently represent a hydrogen atom, an alkyl group having 1 to 8 carbon atoms which may be substituted, an aryl group having 6 to 20 carbon atoms which may be substituted, an arylalkyl group having 7 to 20 carbon atoms which may be substituted, a nitro group, an amino group, a halogen atom, a cyano group, or a heterocyclic group having 2 to 20 carbon atoms; $R^{13}$ and $R^{14}$ each independently represent a hydrogen atom, an alkyl group having 1 to 8 carbon atoms, an aryl group having 6 to 20 carbon atoms, an arylalkyl group having 7 to 20 carbon atoms, or a substituent represented by the following general formula (IV); s and t are each independently an integer from 1 to 5; a methylene group of the alkyl group having 1 to 8 carbon atoms may be replaced by —O— or —CH=CH—,

[Formula 4]

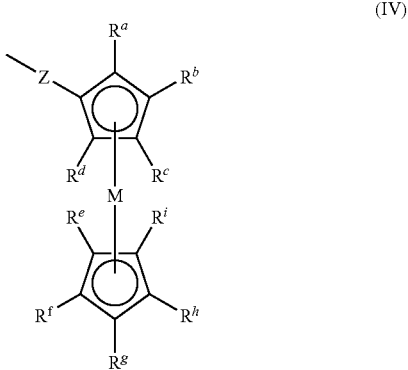

(IV)

wherein $R^a$ to $R^i$ each independently represent a hydrogen atom, a hydroxyl group, or an alkyl group having 1 to 4 carbon atoms, where a methylene group of the alkyl group may be replaced by —O— or —CO—; Z represents a direct bond or an alkylene group having 1 to 8 carbon atoms which may be substituted, where a methylene group of the alkylene group may be replaced by —O—, —S—, —CO—, —COO—, —OCO—, —SO$_2$—, —NH—, —CONH—, —NHCO—, —N=CH—, or —CH=CH—; M represents Fe, Co, Ni, Ti, Cu, Zn, Zr, Cr, Mo, Os, Mn, Ru, Sn, Pd, Rh, Pt, or Ir.

Furthermore, the present invention has accomplished the object by providing an optical filter characterized by containing at least one kind of the above-mentioned compounds.

Also, the present invention has accomplished the object by providing an optical recording material characterized by containing at least one kind of the above-mentioned compounds.

Further, the present invention has accomplished the above-mentioned object by providing an optical recording medium characterized by comprising an optical recording layer disposed on a substrate, the optical recording layer composed of the above-mentioned optical recording material.

BEST MODE FOR CARRYING OUT THE INVENTION

Hereafter, the compound of the present invention, and the optical filter and optical recording material, both containing the compound, will be described in detail based on preferable embodiments.

First, the compound of the present invention represented by the general formula (I), will be described.

With respect to the heterocyclic ring represented by ring A and ring B in the general formula (I), which may be substituted, there is no particular restriction and there may be used a tetrahydropyran, pyran, furan, thiophene, pyrrole, benzofuran, benzothiophene, indole, indolenine, piperidine, piperazine, pyrrolidine, morpholine, thiomorpholine, pyridine, pyrazine, pyrimidine, pyridazine, triazine, quinoline, isoquinoline, imidazole, oxazole, imidazolidine, pyrazolidine, oxazolidine, isoxazolidine, isothiazolidine rings, and the like. These rings may be condensed with other rings or may be substituted.

In the general formula (I), the alkyl group having 1 to 8 carbon atoms which may be substituted, represented by $R^1$ and $R^2$, includes methyl, ethyl, propyl, isopropyl, butyl, sec-butyl, tert-butyl, isobutyl, amyl, isoamyl, tert-amyl, hexyl, cyclohexyl, cyclohexylmethyl, cyclohexylethyl, heptyl, isoheptyl, tert-heptyl, n-octyl, isooctyl, tert-octyl, 2-ethylhexyl, and the like.

In the general formula (I), the ring structure formed by linking of $R^1$ and $R^2$ includes a piperidine, piperazine, pyrrolidine, morpholine, thiomorpholine, pyridine, pyrazine, pyrimidine, pyridazine, triazine, quinoline, isoquinoline, imidazole, oxazole, imidazolidine, pyrazolidine, isoxazolidine, isothiazolidine rings, and the like. These rings may be condensed with other rings or may be substituted.

The benzene, naphthalene, and heterocyclic rings represented by ring A and ring B, and the alkyl group having 1 to 8 carbon atoms represented by $R^1$ and $R^2$ may each have a substituent. As the substituent, the following may be cited, with a note that, when $R^1$ and $R^2$ are groups containing carbon atoms such as the alkyl groups having 1 to 8 carbon atoms and the like, and when, at the same time, those groups possess substituents having carbon atoms among the following substituents, the total number of carbon atoms of $R^1$ or $R^2$ including those of the substituents is required to satisfy the specified ranges.

The above-mentioned substituents include, for example, an alkyl group such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, decyl, and the like; an alkoxy group such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, decyloxy, and the like; an alkylthio group such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, 2-ethylhexylthio, and the like; an alkenyl group such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicocenyl, tricocenyl, and the like; an arylalkyl group such as benzyl, phenethyl, diphenylmethyl, triphenylmethyl, styryl, cinnamyl, and the like; an aryl group such as phenyl, naphthyl, and the like; an aryloxy group such as phenoxy, naphthyloxy, and the like; an arylthio group such as phenylthio, naphthylthio, and the like; a heterocyclic group such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinone-1-yl, 2-piperidone-1-yl, 2,4-dioxyimidazolidine-3-yl, 2,4-dioxyoxazolidine-3-yl, and the like; a halogen atom such as fluorine, chlorine, bromine, iodine, and the like; an acyl group such as acetyl, 2-chloroacetyl, propionyl, octanoyl, acryloyl, methacryloyl, phenylcarbonyl(benzoyl), phthaloyl, 4-trifluoromethylbenzoyl, pivaloyl, salicyloyl, oxaloyl, stearoyl, methoxycarbonyl, ethoxycarbonyl, tert-butoxycarbonyl, n-octadecyloxycarbonyl, carbamoyl, and the like; an acyloxy group such as acetyloxy, benzoyloxy, and the like; a substituted amino group such as amino, ethylmino, dimethylamino, diethylamino, butylamino, cyclopentylamino, 2-ethylhexylamino, dodecylamino, anilino, chlorophenylamino, toluidino, anicidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoyl amino, N,N-dimethylaminocarbonylamino, N,N-diethylaminocarbonylamino, morpholinocarbonylamino, methoxycarbonylamino, ethoxycarbonylamino, tert-butoxycarbonylamino, n-octadecyloxycarbonylamino, N-methyl-methoxycarbonylamino, phenoxycarbonylamino, sulfamoylamino, N,N-dimethylaminosulfonyamino, methylsulfonylamino, butylsulfonylamino, phenylsulfonylamino, and the like; a sulfonamide, sulfonyl, carboxyl, cyano, sulfo, hydroxy, nitro, mercapto, imide, carbamoyl, sulfonamide groups, and the like. These groups may be further substituted. In addition, the carboxyl and sulfo groups may be in the form of salts.

In the general formula (I), the anion represented by $An^{q-}$ includes, as a monovalent anion, for example, a halide ion such as chloride, bromide, iodide, fluoride and the like; an inorganic anion such as perchlorate, chlorate, thiocyanate, hexafluorophosphate, hexafluoroantimonate, tetrafluoroborate, and the like; an organic sulfonate ion such as benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate, and sulfonates described in Japanese Patent Laid-Open Publication No. H8-253705, Japanese Patent Application Laid-Open No. 2004-503379, Japanese Patent Laid-Open Publication No. 2005-336150, International Publication No. WO/2006/28006, and the like; an organic phosphate-related ion such as octyl phosphate, dodecyl phosphate, octadecyl phosphate, phenyl phosphate, nonylphenyl phosphate, 2,2'-methylenebis (4,6-di-tert-butylphenyl) phosphonate, and the like; bistrifluoromethylsulfonylimide; bisperfluorobutanesulfonylimide; perfluoro-4-ethylcyclohexanesulfonate; tetrakis (pentafluorophenyl)borate; tetrakis(pentafluorophenyl) galliumanion; tris(fluoroalkylsulfonyl) carbanion; dibenzoyltartarate, and the like. As a divalent anion, for example, there may be cited benzenedisulfonate, naphthalenedisulfonate, and the like. There may also be used, according to necessity, a quencher anion which can deactivate (quench) an active molecule in the exited state as well as an anion of a metallocene compound such as ferrocene, ruthenocene, and the like, having an anionizable group such as carboxylic acid, phosphoric acid, and sulfonic acid groups on the cyclopentadienyl ring.

The above-mentioned quencher anion includes, for example, those represented by the following general formula (A) or (B), or formula (C) or (D), or anions described in Japanese Patent Laid-Open Publication Nos. S60-234892, H5-43814, H5-305770, H6-239028, H9-309886, H9-323478, H10-45767, H11-208118, 2000-168237, 2002-201373, 2002-206061, and 2005-297407; Japanese Patent Application Publication No. H7-96334; International Publication No. WO/98/29257, and the like.

[Formula 1]

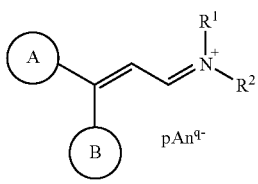

(I)

wherein M represents Fe, Co, Ni, Ti, Cu, Zn, Zr, Cr, Mo, Os, Mn, Ru, Sn, Pd, Rh, Pt, or Ir; $R^9$ and $R^{10}$ represent a halogen atom, an alkyl group having 1 to 8 carbon atoms, an aryl group having 6 to 30 carbon atoms, or a —$SO_2$-G group, G represents an alkyl, aryl that may be substituted with a halogen atom, dialkylamino, diarylamino, piperidino, or morpholino groups; a and b each independently represent an integer from 0 to 4; $R^{11}$, $R^{12}$, $R^{13}$ and $R^{14}$ each independently represent an alkyl, alkylphenyl, alkoxyphenyl, or halogenated phenyl groups.

[Formula 6]

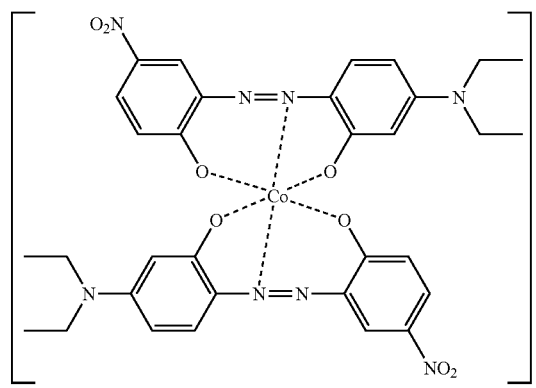

(C)

[Formula 7]

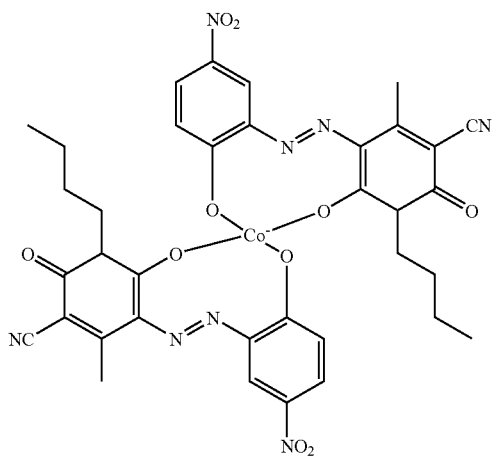

(D)

Among the compounds represented by the general formula (I), those represented by the following general formula (II) or (III) are preferable, because their production costs are low and their absorption wavelength characteristics are especially suitable for formation of an optical recording layer of an optical recording medium for a short wavelength laser light of 380 to 420 nm.

[Formula 8]

[Formula 8]

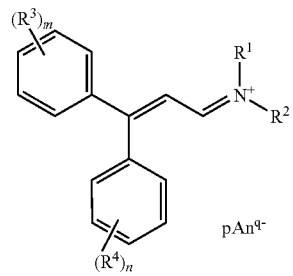

(II)

wherein $R^1$, $R^{2'}$ $An^{q-}$, q, and p are the same as in the general formula (I); $R^3$ and $R^4$ each independently represent a hydrogen atom, an alkyl group having 1 to 8 carbon atoms which may be substituted, an aryl group having 6 to 20 carbon atoms which may be substituted, an arylalkyl group having 7 to 20 carbon atoms which may be substituted, a nitro group, an amino group, a halogen atom, a cyano group, or a heterocyclic group having 2 to 20 carbon atoms; m and n are each independently an integer from 1 to 5; a methylene group of the alkyl group having 1 to 8 carbon atoms may be replaced by —O— or —CH=CH—.

[Formula 9]

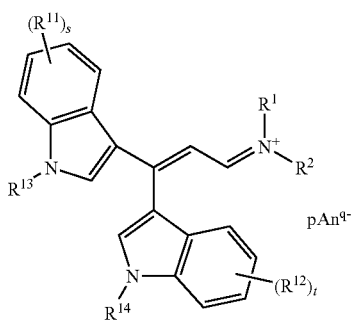

(III)

wherein $R^1$, $R^{2'}$ $An^{q-}$, q, and p are the same as in the general formula (I); $R^{11}$ and $R^{12}$ each independently represent a hydrogen atom, an alkyl group having 1 to 8 carbon atoms which may be substituted, an aryl group having 6 to 20 carbon atoms which may be substituted, an arylalkyl group having 7 to 20 carbon atoms which may be substituted, a nitro group, an amino group, a halogen atom, a cyano group, or a heterocyclic group having 2 to 20 carbon atoms; $R^{13}$ and $R^{14}$ each independently represent a hydrogen atom, an alkyl group having 1 to 8 carbon atoms, an aryl group having 6 to 20 carbon atoms, an arylalkyl group having 7 to 20 carbon atoms, or a substituent represented by the following general formula (IV); s and t are each independently an integer from 1 to 5; a methylene group of the alkyl group having 1 to 8 carbon atoms may be replaced by —O— or —CH=CH—,

[Formula 10]

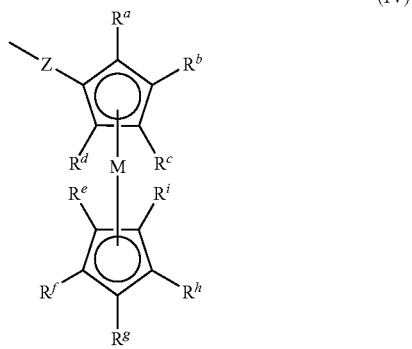

(IV)

wherein $R^a$ to $R^i$ each independently represent a hydrogen atom, a hydroxyl group, or an alkyl group having 1 to 4 carbon atoms, where a methylene group of the alkyl group may be replaced by —O— or —CO—; Z represents a direct bond or an alkylene group having 1 to 8 carbon atoms which may be substituted, where a methylene group of the alkylene group may be replaced by —O—, —S—, —CO—, —COO—, —COO—, —SO$_2$—, —NH—, —CONH—, —NHCO—, —N=CH—, or —CH=CH—; M represents Fe, Co, Ni, Ti, Cu, Zn, Zr, Cr, Mo, Os, Mn, Ru, Sn, Pd, Rh, Pt, or Ir.

The alkyl group having 1 to 8 carbon atoms which may have a substituent, represented by $R^3$ and $R^4$ in the general formula (II) and $R^{11}$, $R^{12}$, $R^{13}$, and $R^{14}$ in the general formula (III), includes those exemplified as $R^3$ and $R^4$ in the general formula (I). The aryl group having 6 to 20 carbon atoms which may have a substituent, represented by $R^3$ and $R^4$ in the general formula (II) and $R^{11}$, $R^{12}$, $R^{13}$, and $R^{14}$ in the general formula (III), includes phenyl, naphthyl, anthracen-1-yl, phenanthren-1-yl, and the like. And the arylalkyl group having 7 to 20 carbon atoms which may have a substituent, represented by $R^3$ and $R^4$ in the general formula (II) and $R^{11}$, $R^{12}$, $R^{13}$, and $R^{14}$ in the general formula (III), includes benzyl, phenethyl, 2-phenylpropane, diphenylmethyl, triphenylmethyl, styryl, cinnamyl, and the like.

The halogen atom represented by $R^3$ and $R^4$ in the general formula (II) and $R^{11}$ and $R^{12}$ in the general formula (III) includes fluorine, chlorine, bromine, iodine, and the like; the heterocyclic group having 2 to 20 carbon atoms, represented by $R^3$ and $R^4$ in the general formula (II) and $R^{11}$ and $R^{12}$ in the general formula (III) includes pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, 2,4-dioxyoxazolidin-3-yl, and the like.

In the general formula (IV), the alkyl group having 1 to 4 carbon atoms, represented by $R^a$ to $R^i$, includes methyl, ethyl, propyl, isopropyl, butyl, sec-butyl, tert-butyl, isobutyl, and the like; the group wherein the methylene group of the alkyl group above is replaced by —O— includes methoxy, ethoxy, propyloxy, isopropyloxy, methoxymethyl, ethoxymethyl, 2-methoxyethyl, and the like; the group wherein the methylene group of the alkyl group above is replaced by —CO— includes acetyl, 1-carbonylethyl, acetylmethyl, 1-carbonylpropyl, 2-oxobutyl, 2-acetylethyl, 1-carbonylisopropyl, and the like. In the general formula (IV), the alkylene group having 1 to 8 carbon atoms which may have a substituent, represented by Z, includes methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, propane-2,2-diyl, and the like; the group wherein the methylene group of the alkylene group above is replaced by —O—, —S—, —CO—, —COO—, —OCO—, —SO$_2$—, —NH—, —CONH—, —NHCO—, —N=CH—, or CH=CH— includes methyleneoxy, ethyleneoxy, oxymethylene, thiomethylene, carbonylmethylene, carbonyloxymethylene, methylenecarbonyloxy, sulfonylmethylene, aminomethylene, acetylamino, ethylene carboxamide, ethane imide-yl, ethenylene, propenylene, and the like.

The alkyl group having 1 to 8 carbon atoms represented by $R^3$ and $R^4$ in the general formula (II) and $R^{11}$, $R^{12}$, $R^{13}$, and $R^{14}$ in the general formula (III), the aryl group having 6 to 20 carbon atoms represented by $R^3$ and $R^4$ in the general formula (II) and $R^{11}$, $R^{12}$, $R^{13}$, and $R^{14}$ in the general formula (III), the arylalkyl group having 7 to 20 carbon atoms represented by $R^{11}$, $R^{12}$, $R^{13}$, and $R^{14}$ in the general formula (III), the amino group represented by $R^3$ and $R^4$ in the general formula (II) and $R^{11}$ and $R^{12}$ in the general formula (III), the heterocyclic group represented by $R^3$ and $R^4$ in the general formula (II) and $R^{11}$ and $R^{12}$ in the general formula (III), and the alkylene group having 1 to 8 carbon atoms represented by Z in the general formula (IV) may each have substituents. The substituents include those exemplified above.

The specific examples of the compound represented by the general formula (I) include the following compounds Nos. 1 to 16. Here, the compounds are shown by the cations, omitting the anions. In the compounds of the present invention, the double bonds may take resonance structures.

[Formula 11]

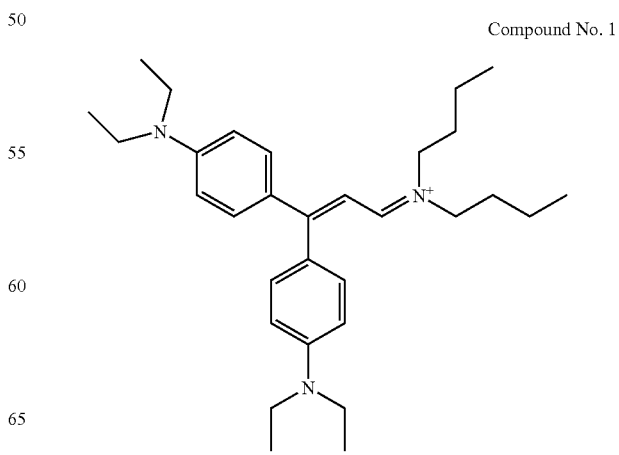

Compound No. 1

-continued
Compound No. 2
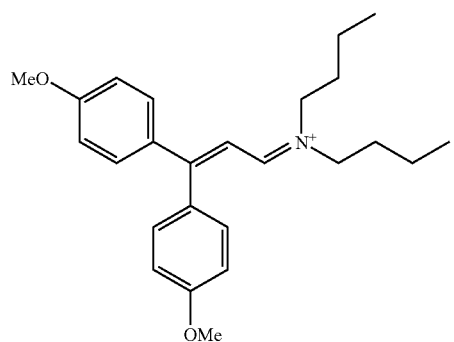
Compound No. 3
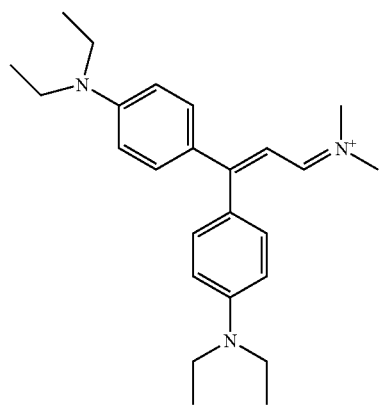
Compound No. 4
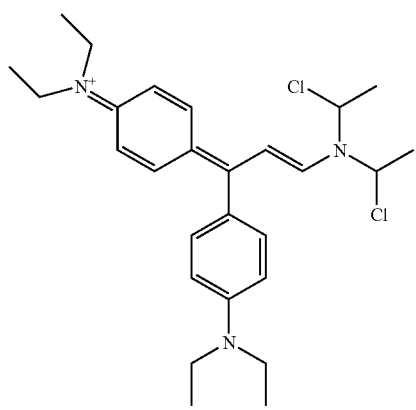
Compound No. 5
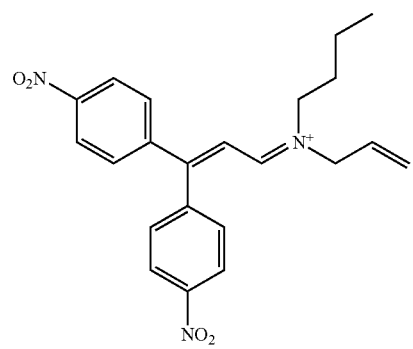
-continued
Compound No. 6
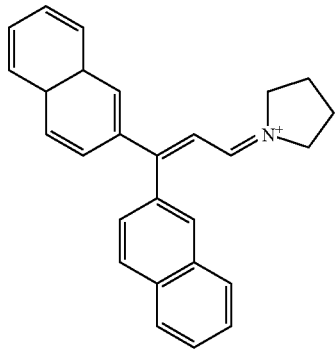
Compound No. 7
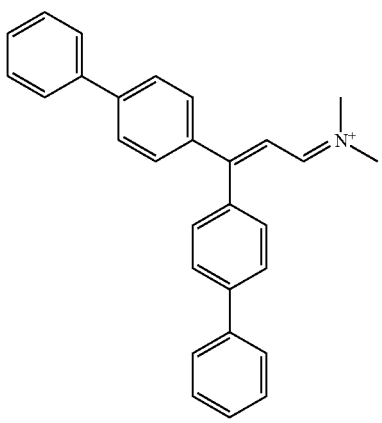
Compound No. 8
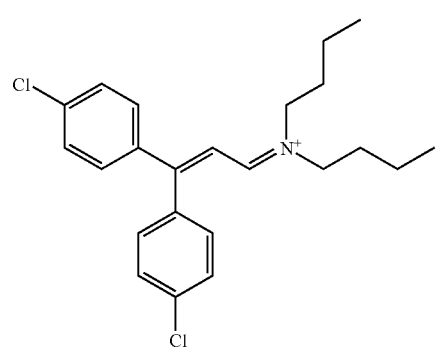
Compound No. 9
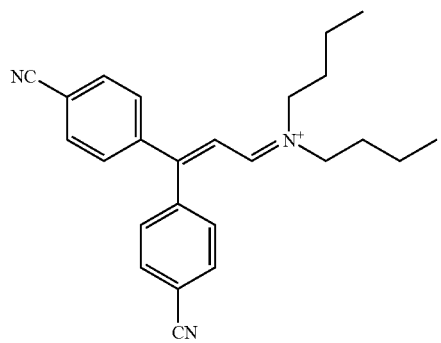

-continued

Compound No. 10

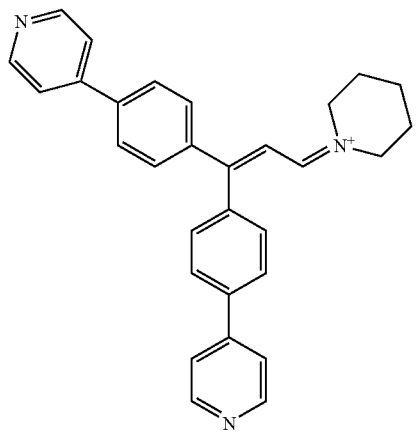

Compound No, 11

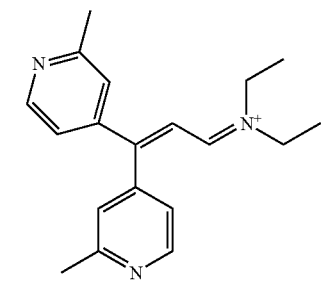

Compound No. 12

[Formula 12 ]

Compound No. 13

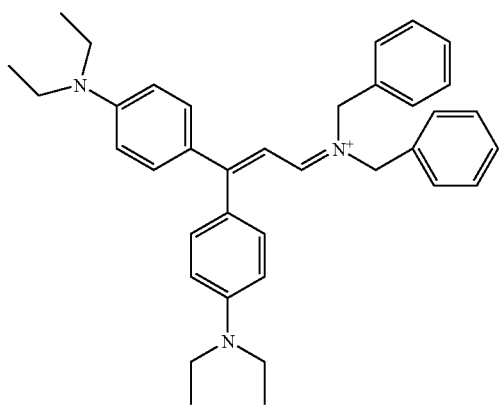

-continued

Compound No. 14

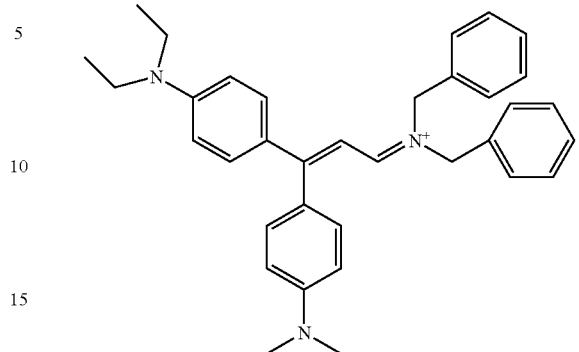

Compound No. 15

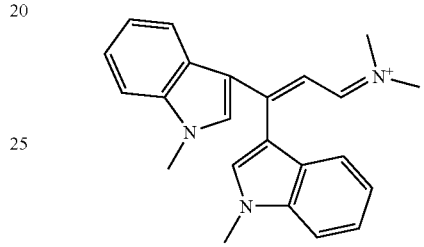

Compound No. 16

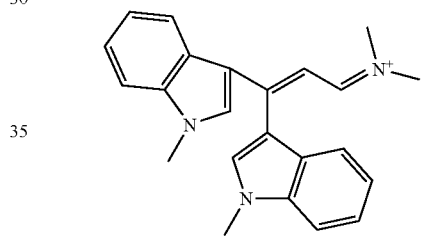

The compound represented by the general formula (I) is not particularly restricted by the method of manufacture and can be obtained by a method utilizing the generally known reactions. The compound may be synthesized by a method wherein a ketone and methylmagnesium bromide are reacted by a Grignard reaction as the reaction shown in the formula (13) below, followed by dehydration to afford an ethene compound. The ethene compound obtained is reacted with a formamide derivative to synthesize the desired compound.

[Formula 13]

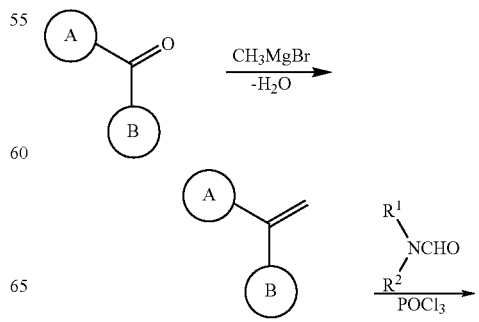

-continued

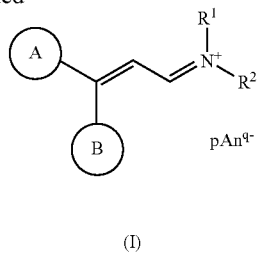

(I)

wherein, ring A, ring B, $R^1$, $R^2$ $An^{q-}$, q and p are the same as in the general formula (I) above.

The above-mentioned compounds of the present invention are suitable as optical elements for light in a range of 450 nm to 1,100 nm, especially for light in a range of 480 nm to 620 nm. The optical elements refer to those which exhibit functions upon absorption of particular light and specifically include a light absorber, an optical recording agent, a photosensitizer, and the like. For example, the optical recording agent is used in the optical recording layers of optical recording media such as DVD±R and the like. The light absorber is used in optical filters for image display units such as liquid crystal displays (LCD), plasma display panels (PDP), electroluminescence displays (ELD), cathode ray tube displays (CRT), fluorescent displays, field emission displays; analytical instruments; semiconductor element manufacturing; astronomical observations; optical communications; and the like.

Next, the optical filter of the present invention containing at least one kind of the compounds of the invention, represented by the general formula (I), will be described in the following.

The amount of the compound of the present invention included in the optical filter of the invention per unit area is, especially for an image display unit, usually 1 to 1,000 mg/m², preferably 5 to 100 mg/m². When the amount used is less than 1 mg/m², a sufficient light absorbing effect is not exhibited and, when an amount exceeding 1,000 mg/m² is used, there are fears that the color tone of the filter becomes so strong that the display quality and the like may be harmed, and, further, that the brightness may be lowered.

When used for an image display unit, the optical filter of the present invention is placed on the front surface. For example, the optical filter of the invention may be pasted directly on the surface of the display or, when there is a front plate placed in front of the display, the optical filter may be pasted on the frontside (outside) or backside (display side) of the front plate.

When used for an image display unit, there may be added to the optical filter of the present invention a light absorber other than the compound of the invention in order to adjust the color tone and the like. There may also be added a light absorber other than the compound of the invention, which can correspond to light between 480 and 500 nm, in order to prevent the reflection or glare of outside light. Further, when the image display unit is a plasma display, there may be added a near infrared light absorber which can correspond to light between 750 and 1,100 nm.

The above-mentioned light absorber for color tone adjustment includes, as one used to remove orange light between 550 and 600 nm, trimethine cyanine derivatives such as trimethine indolium compounds, trimethine benzoxazolium compounds, trimethine benzothiazolium compounds, and the like; pentamethine cyanine derivatives such as pentamethine oxazolium compounds, pentamethine thiazolium compounds, and the like; squarylium dye derivatives; azomethine dye derivatives; xanthene dye derivatives; azo dye derivatives; pyrromethene dye derivatives; azo metal complex derivatives; rhodamine dye derivatives; phthalocyanine derivatives; porphyrin derivatives; dipyrromethene metal chelate compounds; and the like.

Also, the above-mentioned light absorber for preventing glare of outside light, corresponding to light between 480 and 500 nm, includes trimethine cyanine derivatives such as trimethine indolium compounds, trimethine oxazolium compounds, trimethine thiazolium compounds, indolidene trimethine thiazolium compounds, and the like; phthalocyanine derivatives; naphthalocyanine derivatives; porphyrin derivatives; dipyrromethene metal chelate compounds; and the like.

Further, the near infrared light absorber for preventing malfunction of an infrared remote control, corresponding to light between 750 and 1,100 nm, includes i derivatives; pentamethine cyanine derivatives such as pentamethine benzoindolium compounds, pentamethine benzoxazolium compounds, pentamethine benzothiazolium compounds, and the like; heptamethine cyanine derivatives such as heptamethine indolium compounds, heptamethine benzoindolium compounds, heptamethine oxazolium compounds, heptamethine benzoxazolium compounds, heptamethine thiazolium compounds, heptamethine benzothiazolium compounds, and the like; squarylium derivatives; nickel complexes such as bis (stilbenedithiolato) compounds, bis(benzenedithiolato) nickel compounds, bis(carnphordithiolato)nickel compounds, and the like; squarylium derivatives; azo dye derivatives; phthalocyanine derivatives; porphyrin derivatives; dipyrromethene metal chelate compounds; and the like.

In the optical filter of the present invention, the above-mentioned light absorber for color tone adjustment, the light absorber corresponding to light between 480 and 500 nm, and near infrared light absorber may be included in the same layer as the compound of the present invention or in a different layer. The amount of these compounds used per unit area of the optical filter is ordinarily in a range of 1 to 1,000 mg/m², preferably 5 to 100 mg/m².

A representative structure of the optical filter of the present invention comprises a transparent substrate, and, according to necessity, such layers disposed thereon as a primer layer, anti-reflection layer, hard coat layer, lubrication layer, and the like. As a method to have the compound of the present invention and optional ingredients which are dye compounds other than the compound of the invention such as the light absorbers and various stabilizers included in the optical filter of the present invention, there may be mentioned, for example, (1) a method wherein the compounds are included in the transparent substrate or any optional layer, (2) a method wherein the compounds are coated on the transparent substrate or any optional layer, (3) a method wherein the compounds are included in the adhesive layer between any two neighboring members selected from the transparent substrate and any optional layer, (4) a method wherein a light absorbing layer is formed separately from any optional layer, the light absorbing layer including the light absorber and the like such as the compounds of the present invention and the like. The compounds of the present invention may suitably be included in the adhesive layer according to the method (3) above or may be included in the light absorbing material according to the method (4) above.

The materials for the transparent substrate include, for example, inorganic materials such as glass and the like; polymeric materials including cellulose esters such as diacetyl cellulose, triacetyl cellulose (TAC), propionyl cellulose, butyryl cellulose, acetyl propionyl cellulose, nitrocellulose, and the like; polyamides; polycarbonate; polyesters such as polyethylene terephthalate, polyethylene naphthalate, polybutylene terephthalate, poly-(1,4-cyclohexanedimethylene terephthalate), polyethylene-1,2-diphenoxyethane-4,4'-dicarboxylate, polybutylene terephthalate, and the like; polystyrene; polyolefins such as polyethylene, polypropylene, polymethylpentene, and the like; acrylic resins such as polymethyl methacrylate and the like; polycarbonate; polysulfone; polyethersulfone, polyether ketone; polyether imide; and polyoxyethylene, norbornene resin, and the like. The transmittance of the transparent substrate is preferably 80% or higher, more preferably 86% or higher. The haze is preferably 2% or less, more preferably 1% or less. The refractive index is preferably between 1.45 and 1.70.

To the transparent substrate may be added infrared light absorbers, ultraviolet light absorbers, antioxidants of phenol-, phosphorous-, and other types, flame retardants, lubricants, antistatic agents, inorganic micro particles, and the like. The transparent substrate may be provided with various surface treatments.

The above-mentioned inorganic micro particles include silicon dioxide, titanium dioxide, barium sulfate, calcium carbonate, talc, kaolin, and the like.

The above-mentioned various surface treatments include, for example, a chemical treatment, mechanical treatment, corona discharge treatment, flame treatment, ultraviolet radiation treatment, high frequency wave treatment, glow discharge treatment, active plasma treatment, laser treatment, mixed acid treatment, ozone oxidation treatment, and the like.

The above-mentioned primer layer is a layer formed between the transparent substrate and the light absorbing layer, when a light absorbing layer containing the light absorber is formed. The primer layer is formed as a layer containing a polymer with a glass transition temperature between −60 and 60° C., as a layer with a rough surface facing the light absorbing layer, or as a layer comprising a polymer which is compatible with the polymer contained in the light absorbing layer. Also, the primer layer may be formed on the surface of a transparent substrate on which the light absorbing layer is not formed, in order to improve adhesion between the substrate and a layer formed thereon (for example, an anti-reflection layer or a hard coat layer) or in order to improve affinity between the adhesive and the optical filter, the adhesive being used for adhesion of the optical filter and the image display unit. The thickness of the primer layer is preferably 2 nm to 20 μm, more preferably 5 nm to 5 μm, even more preferably 20 nm to 2 μm, still more preferably 50 nm to 1 μm, most preferably 80 nm to 300 nm. The primer layer composed of a polymer with a glass transition temperature between −60 to 60° C. enables adhesion of the transparent substrate and the filter layer due to tackiness of the polymer. The polymer with a glass transition temperature between −60 to 60° C. is obtained, for example, by polymerization or copolymerization of vinyl chloride, vinylidene chloride, vinyl acetate, butadiene, neoprene, styrene, chloroprene, an acrylic acid ester, a methacrylic acid ester, acrylonitrile, or methyl vinyl ether. The glass transition temperature is preferably 50° C. or lower, more preferably 40° C. or lower, even more preferably 30° C. or lower, still more preferably 25° C. or lower, most preferably 20° C. or lower. The elastic modulus at 25° C. of the primer layer is preferably between 1 to 1,000 MPa, more preferably between 5 to 800 MPa, most preferably 10 to 500 MPa. The primer layer with a rough surface facing the light absorbing layer enables adhesion of the transparent substrate and the light absorbing layer by forming the light absorbing layer on its rough surface. The primer layer with a rough surface facing the light absorbing layer is easily formed by coating a polymer latex. The average particle size of the latex is preferably 0.02 to 3 μm, more preferably 0.05 to 1 μm. The polymer which is compatible with the binder polymer of the light absorbing layer includes acrylic resins, cellulose derivatives, gelatin, casein, starch, polyvinyl alcohol, soluble nylon, polymer latexes, and the like. In addition, the optical filter of the present invention may have two or more primer layers. To the primer layer, there may be added a solvent which swells the transparent substrate, matting agent, surfactant, antistatic agent, coating aid, hardener, and the like.

In the above-mentioned anti-reflection layer, a low refractive index layer is essential. The refractive index of the low refractive index layer is lower than the refractive index of the transparent substrate above. The refractive index of the low refractive index layer is preferably 1.20 to 1.55, more preferably 1.30 to 1.50. The thickness of the low refractive layer is preferably 50 to 400 nm, more preferably 50 to 200 nm. The low refractive index layer may be formed as a layer composed of a low refractive index, fluorine-containing polymer (described in each of Japanese Patent Laid-Open Publication Nos. S57-34526, H3-130103, H6-115023, H8-313702, H7-168004), as a layer obtained by a sol-gel method (described in each of Japanese Patent Laid-Open Publication Nos. H5-208811, H6-299091, H7-168003), or as a layer composed of micro particles (described in each of Japanese Patent Application Publication No. S60-59250, Japanese Patent Laid-Open Publication Nos. H5-13021, H6-56478, H7-92306, H9-288201). In the layer composed of micro particles, there may be formed in the low refractive index layer voids which are formed as micro-voids between the micro particles or inside the micro particles. The layer composed of the micro particles has a void fraction of preferably 3 to 50% by volume, more preferably 5 to 35% by volume.

In order to prevent reflection of light of a wide range of wavelength, it is preferable for the above-mentioned anti-reflection layer to have a higher refractive index layer (a medium or high refractive index layer) laminated, in addition to the low refractive index layer. The refractive index of the high refractive index layer is preferably 1.65 to 2.40, more preferably 1.70 to 2.20. The refractive index of the medium refractive index layer is adjusted so that it acquires an intermediate value between the refractive indices of the low refractive index layer and high refractive index layer. The refractive index of the medium refractive index layer is preferably 1.50 to 1.90, more preferably 1.55 to 1.70. The thickness of the medium or high refractive index layer is preferably 5 nm to 100 μm, more preferably 10 nm to 10 μm, most preferably 30 nm to 1 μm. Haze of the medium or high refractive index layer is preferably 5% or less, more preferably 3% or less, most preferably 1% or less. The medium or high refractive index layer may be formed using a polymer binder with a relatively high refractive index. The high refractive index polymer includes polystyrene, a styrene copolymer, polycarbonate, melamine resin, phenol resin, epoxy resin, polyurethane obtained by a reaction of cyclic (cycloaliphatic or aromatic) isocyanate and polyol, and the like. Other polymers containing cyclic (aromatic, heterocyclic, alicyclic) groups as well as polymers containing halogen atoms other than fluorine as substituents have high refractive indices. It is also possible to use polymers formed by polymerization of monomers which were made free radically curable by introduction of double bonds.

In order to obtain even higher refractive index, there may be dispersed inorganic micro particles in the above-mentioned polymer binders. The refractive indices of the inorganic micro particles are preferably between 1.80 and 2.80.

The inorganic micro particles are preferably formed from metal oxides or metal sulfides. The metal oxides or metal sulfides include titanium oxide (for example, rutile, rutile/anatase mixed crystal, anatase, amorphous structure), tin oxide, indium oxide, zinc oxide, zirconium oxide, zinc sulfide, and the like. Among these, titanium oxide, tin oxide, and indium oxide are especially preferable. With these metal oxides or sulfides as the main component, the inorganic micro particles may further include other elements. Here, the main component refers to a component of the largest content (in % by weight) among the components which constitute the particles. Other elements include Ti, Zr, Sn, Sb, Cu, Fe, Mn, Pb, Cd, As, Cr, Hg, Zn, Al, Mg, Si, P, S, and the like. The medium or high refractive index layer may also be formed by use of an inorganic material which may disperse in solvents with a film forming property or is a liquid by itself, with examples including alkoxides of various elements, salts of organic acids, coordination compounds (for example, chelate compounds) bonded with coordinating compounds, or active inorganic polymers.

On the surface of the above-mentioned anti-reflection layer, there may be provided an anti-glare function (a function to prevent the surrounding scenery reflected on the film surface by scattering the incident light on the surface). For example, anti-reflection layer having an anti-glare function can be obtained by forming micro asperities on the transparent film, followed by formation of an anti-reflection layer thereon, or, after formation of the anti-reflection layer, by forming asperities on the surface by an emboss roll. The anti-reflection layer with an anti-glare function generally has a haze of 3 to 30%.

The above-mentioned hard coat layer has higher hardness than that of the transparent substrate. The hard coat layer preferably contains a crosslinked polymer. The hard coat layer can be formed using acrylic, urethane, or epoxy-based polymers, oligomers, monomers (for example, an ultraviolet light curable resin), or the like. It is also possible to form a hard coat layer from a silica-based material.

On the surface of the above-mentioned anti-reflection layer (the low refractive index layer), there may be formed a lubrication layer. The lubrication layer imparts a lubricating property to the surface of the low refractive index layer and exhibits a function to improve scratch resistance. The lubrication layer may be formed using polyorganosiloxane (for example, silicone oil), natural wax, petroleum wax, a higher fatty acid metal salt, or a fluorine-based lubricant or its derivative. The thickness of the lubrication layer is preferably 2 to 20 nm.

When the aforementioned "(3) method wherein the compounds are included in the adhesive layer between any two neighboring layers selected from the transparent substrate and any optional layer" is employed in order to include the compound of the present invention into the optical filter, the compound of the present invention is first included in the adhesive and, then, using the adhesive, any two neighboring members selected from the transparent substrate and optional layers are adhered. As the adhesive, those publicly known as a transparent adhesive for laminated glass may be used, which is based on silicones, urethanes, acrylics, polyvinyl butyral, ethylene vinyl acetate, and the like. Also, when using the adhesive, a cross-linking agent based on metal chelates, isocyanates, epoxies, and the like may be used as a curing agent. Further, the thickness of the adhesive layer is preferably 2 to 400 μm.

When the aforementioned "(4) method wherein a light absorbing layer is formed separately from any optional layer, the light absorbing layer including the light absorber and the like such as the compound of the present invention and the like" is employed, the compound of the present invention is used as it is to form the light absorbing layer or is dispersed in a binder to form the light absorbing layer. The binder includes, for example, a natural polymeric material such as gelatin, casein, starch, cellulose derivatives, alginic acid, and the like; or a synthetic polymeric material such as polymethyl methacrylate, polyvinyl butyral, polyvinyl pyrrolidone, polyvinyl alcohol, polyvinyl chloride, a styrene-butadiene copolymer, polystyrene, polycarbonate, polyamide, and the like.

In using the above-mentioned binder, an organic solvent may be used at the same time. As the organic solvent, publicly known various solvents may be used as appropriate without any particular restriction. The solvents include, for example, a alcohol such as isopropanol and the like; an ether alcohol such as methyl cellosolve, ethyl cellosolve, butyl cellosolve, butyl diglycol, and the like; a ketone such as acetone, methyl ethyl ketone, methyl isobutyl ketone, cyclohexanone, diacetone alcohol, and the like; an ester such as ethyl acetate, butyl acetate, methoxyethyl acetate, and the like; an acrylic acid ester such as ethyl acrylate, butyl acrylate, and the like; a fluorinated alcohol such as 2,2,3,3-tetrafluoropropanol and the like; a hydrocarbon such as hexane, benzene, toluene, xylene, and the like; a chlorinated hydrocarbon such as methylene dichloride, dichloroethane, chloroform, and the like. These organic solvents may be used independently or as a mixture.

Further, the aforementioned primer layer, anti-reflection layer, hard coat layer, lubrication layer, light absorbing layer, and the like may be formed by general coating methods. The coating methods include a dip coating, air-knife coating, curtain coating, roller coating, wire bar coating, gravure coating, extrusion coating using a hopper (U.S. Pat. No. 2,681,294), and the like. Two or more layers may be formed by simultaneous coating. The simultaneous coating method is described in each of U.S. Pat. Nos. 2,761,791, 2,941,898, 3,508,947, and 3526528, and in "Coating Kougaku", by Yuji Harazaki, Asakura Shoten, Tokyo, Japan (1973), p 253.

Next, the optical recording material of the present invention comprising the compound of the invention will be described in the following, the material being used in an optical recording layer of an optical recording medium wherein the optical recording layer is formed on a substrate.

The compound of the present invention represented by the general formula (I) is also useful for an optical recording material used in an optical recording layer of an optical recording medium, wherein information is recorded as thermal information patterns provided by means of a laser and the like. The compound is especially suitable for an optical recording material used in optical recording layers of DVD-R, DVD+R, and the like. In addition, the optical recording material of the present invention is a material used to form the optical recording layer and refers to a mixture of the compound of the present invention represented by the general formula (I), and organic solvents and various compounds which will be described later.

There is no particular restriction on the method of forming an optical recording layer of an optical recording medium using the optical recording material of the present invention, which contains the compound represented by the general formula (I). Generally, the compound of the present invention and, if necessary, various compounds described later are dissolved in an organic solvent to prepare the optical recording material as a solution, the organic solvent including a lower alcohol such as methanol, ethanol, and the like; an ether alcohol such as methyl cellosolve, ethyl cellosolve, butyl cellosolve, butyl diglycol, and the like; a ketone such as acetone, methyl ethyl ketone, methyl isobutyl ketone, cyclohexanone, diacetone alcohol, and the like; an ester such as ethyl acetate, butyl acetate, methoxyethyl acetate, and the like; an acrylic acid ester such as ethyl acrylate, butyl acrylate, and the like; fluorinated alcohols such as 2,2,3,3-tetrafluoropropanol and the like; a hydrocarbon such as benzene, toluene, xylene, and the like; a chlorinated hydrocarbon such as methylene dichloride, dichloroethane, chloroform, and the like. The optical recording material is coated on a substrate by a wet coating method including spin coating, spraying, dipping, and the like. Methods such as vapor deposition, sputtering, and the like may also be employed. When using the above-mentioned organic solvent, the amount used is preferably such that the content of the compound represented by the general formula (I) becomes 0.1 to 10% by mass of the optical recording material of the present invention.

The optical recording layer is formed as a thin film and its suitable thickness is usually 0.001 to 10 μm, preferably in a range of 0.01 to 5 μm.

Further, in the optical recording material of the present invention, the content of the compound represented by the general formula (I) is preferably 10 to 100% by mass of the solids contained in the optical recording material. The optical recording layer is preferably formed in such a way that the content of the compound represented by the general formula (I) is 50 to 100% by mass of the optical recording layer. To form an optical recording layer of such a content of the compound, the optical recording material of the present invention more preferably contains the compound represented by the general formula (I) in an amount of 50 to 100% by mass based on the solid content of the optical recording material of the invention.

The above-mentioned solid content of the optical recording material of the present invention refers to the components left after removing the components other than the solid content, namely, the solvent and the like, from the optical recording material. The solid content of the optical recording material is preferably 0.01 to 100% by mass, more preferably 0.1 to 10% by mass.

In addition to the compound of the present invention, the optical recording material of the present invention may contain, according to necessity, a compound usually used for an optical recording layer such as azo compounds, phthalocyanines, oxonols, squarylium compounds, indoles, styryl compounds, porphyns, azlenium compounds, chroconicmethines, pyrylium compounds, thiopyrylium compounds, triarylmethanes, diphenylmethanes, tetrahydrocholines, indophenols, anthraquinones, naphthoquinones, xanthene compounds, thiazines, acridines, oxazines, spiropyrans, fluorenes, rhodamines, and the like; a resin such as polyethylene, polyester, polystyrene, polycarbonate, and the like; a surfactant; an antistatic agent; a lubricating agent; a fire retardant; a radical trapping agent such as a hindered amine; a pit formation acceleraror such as a ferrocene derivative and the like; a dispersant; an antioxidant; a crosslinking agent; a light stability-providing agent, and the like. Further, the optical recording material of the present invention may contain, as a quencher of singlet oxygen and the like, an aromatic nitroso compound, aminium compound, iminium compound, bisiminium compound, transition metal chelate compound, and the like. In the optical recording material of the present invention, these various compounds are used in an amount of 0 to 50% by mass based on the solids contained in the optical recording material of the present invention.

There is no particular restriction on the material used as the substrate on which such an optical recording layer is formed, provided that it is substantially transparent to the writing (recording) light and reading (reproducing) light, examples including resins such as polymethyl methacrylate, polyethylene terephthalate, polycarbonate, and the like; glass and the like. Further, its shape is optionally selected, corresponding to the application, from a tape, drum, belt, disc, and the like.

Further, there may be formed on the optical recording layer a reflection film by a vapor deposition or sputtering method using gold, silver, aluminum, copper, and the like. Also, a protection layer may be formed using an acrylic resin, ultraviolet light curable resin, and the like.

EXAMPLES

Hereafter, the present invention will be described in more detail in terms of Manufacturing Examples and Examples. However, the present invention will not be limited in any way by the following Examples and the like.

The following Manufacturing Examples 1 to 3 show examples of manufacture of ethene compounds which are the raw materials to obtain the compounds represented by the general formula (I), while Examples 1 to 7 show examples of manufacture of the compounds represented by the general formula (I). Examples 8 to 15 show examples of preparation of the optical filters of the present invention, using the compounds of the present invention obtained in Examples 1 and 3.

Also, the following Examples 16 to 22 show examples of optical recording materials and optical recording media of the present invention, using the compounds of the present invention obtained in Examples 1 to 7, while Comparative Example 1 shows an example of an optical recording material and an optical recording medium using a compound having a different structure from the compounds of the present invention. Further, in the following Evaluation Example 1, light resistance of the compounds of the present invention obtained in Examples 2, 5, 6, and 7 as well as a comparative compound was evaluated. In the following Evaluation Example 2, suitability of the optical recording media obtained in Examples 16 to 20 was evaluated for recording and reproduction by short wavelength laser light.

Manufacturing Examples 1 to 3

Manufacture of Ethene Compounds

According to the synthetic method described below, ethene compound 1 [bis(N,N-diethylaminophenyl)ethene], ethene compound 2 [bis(methoxyphenyl)ethene], and ethene compound 3 [bis(N-methylindolyl)ethene] were synthesized. The compounds obtained were identified by $^1$H-NMR analyses (see Table 1).

Synthetic Example

To 49.9 mmol of a ketone compound dissolved in 40 g of toluene in a reaction vessel, 64.4 mmol of a 1.0 mol/l tetrahydrofuran solution of methylmagnesium bromide was added and the reaction mixture was heated under reflux for 1 hour. To this was added dropwise a mixture of 17 g of acetic acid and 17 g of water, and the reaction mixture was heated under reflux for additional 1 hour. After cooling to room temperature, the layers were separated. The organic layer was dried over anhydrous magnesium sulfate, the solvent was removed by distillation, and the residue was purified by recrystallization to obtain the desired ethene compound.

TABLE 1

|  | Ethene compound | ¹H-NMR (DMSO-d6) |
|---|---|---|
| Manufacturing Example 1 | Ethene compound 1 | 7.25 (d, 4H J = 8.8 Hz), 6.62 (d, 4H J = 8.8 Hz), 5.14 (s, 2H), 3.34 (q, 8H, J = 7.1 Hz), 1.15 (t, 12H, J = 7.1 Hz) |
| Manufacturing Example 2 | Ethene compound 2 | 7.27 (d, 4H J = 8.3 Hz), 6.86 (d, 4H J = 8.3 Hz), 5.29 (s, 2H), 3.82 (s, 6H) |
| Manufacturing Example 3 | Ethene compound 3 | 7.76 (d, 2H J = 8.1 Hz), 7.32 (d, 2H J = 8.3 Hz), 7.24 (dd, 2H J = 7.8, 7.3 Hz), 7.10 (dd, 2H J = 7.8, 7.3 Hz), 7.06 (s, 2H), 5.54 (s, 2H), 3.73 (s, 6H) |

Examples 1 to 5

Manufacture of $PF_6$ Salts of the Compounds Represented by the General Formula (I)

According to the synthetic method described below, $PF_6$ salts of compounds Nos. 1 to 3, No. 13, and No. 15 were synthesized. The compounds obtained were identified by IR analyses and ¹H-NMR analyses (see [Table 3] and [Table 4]). In [Table 2] are shown the yields and results of measurement of the characteristic values [light absorption characteristics ($\lambda$max and $\epsilon$ at $\lambda$max) as solutions, melting points, and decomposition points] of the compounds obtained.

It is noted that, in [Table 2], the decomposition point refers to the temperature in the differential thermal analysis performed at a heating rate of 10° C./min, whereat the mass of the sample begins to decrease.

Synthetic Example

Synthesis of $PF_6$ Salts of Compounds Nos. 1 to 3, No. 13, and No. 15

To 23.8 mmol of a formamide derivative placed in a reaction vessel was added dropwise 7.5 mmol of phosphorous oxychloride under ice-bath cooling and the reaction mixture was stirred for 1 hr also under ice-bath cooling. Subsequently, 5.0 mmol of any of the ethene compounds obtained in Manufacturing Examples 1 to 3 was added under ice-bath cooling and the reaction mixture was stirred at 100° C. for 3 hours. To the reaction mixture was added 43.5 mmol of $KPF_6$ and, after mixing, 100 ml each of water and ethyl acetate were added and the layers were separated. The organic layer was dried over anhydrous magnesium sulfate, the solvent was removed by distillation, and the residue was purified by column chromatography or recrystallization. Thus obtained were the desired $PF_6$; salts of compounds Nos. 1 to 3, No. 13, and No. 15.

Examples 6 and 7

Synthesis of Quencher Anion Salts of Compounds Nos. 2 and 3

In a reaction vessel, 5.0 mmol of either of the ethene compounds obtained in Manufacturing Examples 1 and 2 were dissolved in 20 ml of acetone, and to this was added dropwise 5.0 mmol of triethylamine salt of the anion represented by the formula [C] dissolved in 122 ml of acetone. To the reaction mixture was added additional 20 ml of acetone and the mixture was heated under reflux for 3 hours. After the reaction mixture was cooled to room temperature, it was added dropwise to 800 ml of water, and the mixture was stirred for 13 hours at room temperature. The solids which precipitated were collected by filtration and dried. Thus obtained were the desired quencher anion salts of the compounds Nos. 2 and 3

TABLE 2

|  | Compound | Yield (%) | $\lambda$max (nm) | $\epsilon$ ($\times 10^4$) | Melting point (° C.) | Decomposition point (° C.) |
|---|---|---|---|---|---|---|
| Example 1 | $PF_6$ salt of compound No. 1 | 1.6 | 495.5 | 7.68 | 142 | 279 |
| Example 2 | $PF_6$ salt of compound No. 2 | 88 | 404.0 | 3.81 | — | 253 |
| Example 3 | $PF_6$ salt of compound No. 3 | 70 | 490.0 | 7.19 | 161 | 271 |
| Example 4 | $PF_6$ salt of compound No. 13 | 2.5 | 502.0 | 8.27 | — | 269 |
| Example 5 | $PF_6$ salt of compound No. 15 | 70 | 490.0 | 7.19 | 161 | 271 |
| Example 6 | Quencher anion salt of compound No. 2 | 81 | 545.5 | 6.29 | 164 | 253 |
| Example 7 | Quencher anion salt of compound No. 3 | 49 | 502.5 | 12.2 | — | 270 |

TABLE 3

| | Compound | IR absorption spectrum (cm$^{-1}$) |
|---|---|---|
| Example 1 | PF$_6$ salt of compound No. 1 | 2967, 1590, 1410, 1354, 1193, 841 |
| Example 2 | PF$_6$ salt of compound No. 2 | 2960, 1625, 1598, 1573, 1258, 1175, 1028, 841 |
| Example 3 | PF$_6$ salt of compound No. 3 | 2975, 1592, 1508, 1410, 1354, 1270, 1241, 1193, 1142, 839 |
| Example 4 | PF$_6$ salt of compound No. 13 | 1589, 1569, 1411, 1353, 1249, 1190, 1156, 841 |
| Example 5 | PF$_6$ salt of compound No. 15 | 1627, 1518, 1460, 1236, 1081, 839 |
| Example 6 | Quencher anion salt of compound No. 2 | 2967, 1609, 1459, 1389, 1321, 1284, 1261, 1170, 1141, 1072 |
| Example 7 | Quencher anion salt of compound No. 3 | 2971, 1609, 1590, 1466, 1390, 1343, 1321, 1283, 1263, 1141, 1073 |

TABLE 4

| | Compound | $^1$H-NMR (DMSO-d6) |
|---|---|---|
| Example 1 | PF$_6$ salt of compound No. 1 | 7.73 (d, 1H, J = 11.2 Hz), 7.38 (d, 2H, J = 8.8 Hz), 7.13 (d, 2H, J = 8,8 Hz), 6.80 (d, 2H, J = 9.3 Hz), 678 (d, 2H, J = 9.3 (Hz), 6.65 (d, 1H, J = 11.0 Hz), 3.79 (t, 2H, J = 7.6 Hz), 3.65 (t, 2H, J = 7.1 Hz), 3.53-3.38 (m, 8H), 1.80-1.55 (m, 4H), 1.40 (tq, 2H, J = 7.6, 7.6 Hz), 1.29 (tq, 2H, J = 7.6, 7.6 Hz), 1.15 (t, 6H, J = 7.1 Hz), 1.13 (t, 6H, J = 7.1 Hz), 0.95 (t, 3H, J = 7.3 Hz), 0.90 (t, 3H, J = 7.3 Hz) |
| Example 2 | PF$_6$ salt of compound No. 2 | 8.03 (d, 1H, J = 10.7 Hz), 7.51 (d, 2H, J = 8.8 Hz), 7.28 (d, 2H, J = 8.5 Hz), 7.14 (d, 2H, J = 8.5 Hz), 7.12 (d, 1H, J = 10.5 Hz), 7.09 (d, 2H, J = 9.0 Hz), 3.98 (t, 2H, J = 7.8 Hz), 3.89 (s, 3H), 3.86 (s, 3H), 3.80 (t, 2H, 7.6 Hz), 1.82-1.60 (m, 4H), 1.44 (tq, 2H, J = 7.6, 7.6 Hz), 1.30 (tq, 2H, J = 7.6, 7.6) Hz), 0.96 (t, 3H, J = 7.3 Hz), 0.91 (t, 3H, J = 7.3 Hz) |
| Example 3 | PF$_6$ salt of compound No. 3 | 7.78 (d, 1H, J = 11.2 Hz), 7.39 (d, 2H, J = 9.0 Hz), 7.18 (d, 2H, J = 8.5 Hz), 6.90-6.70 (m, 4H), 6.62 (d, 1H, J = 11.0 Hz), 3.53-3.38 (m, 14H), 1.16 (t, 6H, J = 7.1 Hz), 1.14 (t, 6H, 7.1 Hz) |
| Example 4 | PF$_6$ salt of compound No. 13 | 7.97 (d, 1H, J = 11.2 Hz), 7.48-7.33 (m, 10H), 7.31 (d, 2H, J = 9.3 Hz), 7.16 (d, 2H, J = 9.0 Hz), 6.80-6.72 (m, 5H), 5.07 (s, 2H), 4.90 (s, 2H), 3.47 (q, 4H, J = 6.6 Hz), 3.44 (q, 4H, J = 6.8 Hz), 1.17 (t, 6H, J = 7.1 Hz), 1.12 (t, 6H, J = 7.1 Hz) |
| Example 5 | PF$_6$ salt of compound No. 15 | 7.95 (s, 1H), 7.77 (d, 1H, J = 11.0 Hz), 7.70-7.61 (br, 1H), 7.57 (s, 1H), 7.46 (d, 1H, J = 9.0 Hz), 7.44 (d, 1H, J = 9.3 Hz), 7.37 (dd, 1H, J = 8.1, 8.1 Hz), 7.34-7.20 (m, 3H), 7.06 (dd, 1H, J = 7.8, 7.3 Hz), 6.67 (d, 1H, J = 11.0 Hz), 4.01 (s, 3H), 3 85 (s, 3H), 3.47 (s, 3H), 3.42 (s, 3H) |
| Example 6 | Quencher anion salt of compound No. 2 | 9.01 (d, 2H, J = 2.9 Hz), 7.98 (d, 1H, J = 10.7 Hz), 7.85 (dd, 2H, J = 9.3, 2.9 Hz), 7.65 (d, 2H, J = 9.3 Hz), 7.47 (d, 2H, J = 8.8 Hz), 7.25 (d, 2H, J = 8.5 Hz), 7.12 (d, 2H, J = 8.8 Hz), 7.08 (d, 1H, J = 10.7 Hz), 7.06 (d, 2H, J = 8.8 Hz), 6.55 (d, 2H, J = 9.3 Hz), 6.35 (dd, 2H, J = 9.5, 2.7 Hz), 5.74 (d, 2H, J = 2.7 Hz), 3.93 (t, 2H, J = 7.8 Hz), 3.86 (s, 3H), 3.84 (s, 3H), 3.76 (t, 2H, J = 7.3 Hz), 3.50-3.20 (m, 8H), 1.80-1.58 (m, 4H), 1.40 (tq, 2H, J = 7.6, 7.6 Hz), 1.27 (tq, 2H, J = 7.6, 7.3 Hz), 1.01 (t, 12H, J = 6.8 Hz), 0.93 (t, 3H, J = 7.3 Hz), 0.89 (t, 3H, J = 7.3 Hz) |
| Example 7 | Quencher anion salt of compound No. 3 | 9.01 (d, 2H, J = 2.7 Hz), 7.85 (dd, 2H, J = 9.0, 2.7 Hz), 7.76 (d, 1H, J = 11.0 Hz), 7.65 (d, 2H, J = 9.3 Hz), 7.37 (d, 2H, J = 9.0 Hz), 7.15 (d, 2H, J = 8.8 Hz), 6.79 (d, 2H, J = 8.5 Hz), 6.74 (d, 2H, J = 9.0 Hz), 6.57 (d, 1H, J = 10.2 Hz), 6.55 (d, 2H, J = 9.3 Hz), 6.35 (dd, 2H, J = 9.5, 2.4 Hz), 5.74 (d, 2H, J = 2.4 Hz), 3.50-3.38 (m, 14H), 3.29 (q, 8H, J = 6.8 Hz), 1.15 (t, 6H, J = 6.8 Hz), 1.13 (t, 6H, J = 7.1 Hz), 1.019 (t, 12H, J = 7.1 Hz) |

Example 8

Preparation of an Optical Filter

A coating liquid of the following composition was prepared and the liquid was coated on a 188 μm thick, easy-adhesion treated polyethylene terephthalate film by a bar coater No. 9. The coated film was dried at 100° C. for 3 minutes to obtain an optical filter (the content of compound No. 1, 2.0 mg/m$^2$) having a 10 μm thick film layer on a polyethylene terephthalate film. An absorption spectrum of this optical filter was measured by an UV/Vis/NIR spectrophotometer V-570 manufactured by JASCO Corporation to show a λmax at 495 nm with a half bandwidth of 67 nm.

| [Composition] | |
|---|---|
| SUMIPEX LG (An acrylic resin binder manufactured by Sumitomo Chemical Co., Ltd; the resin content, 40% by mass) | 2.5 g |
| $PF_6$ salt of compound No. 1 | 2 mg |
| Methyl ethyl ketone | 2.5 g |

Example 9

Preparation of an Optical Filter 2

An adhesive solution of the following composition was prepared and the solution was coated on a 188 μm thick, easy-adhesion treated polyethylene terephthalate film by a bar coater No. 30. The coated film was dried at 100° C. for 10 minutes to obtain an optical filter (the content of compound No. 1, 2.0 mg/m²) having an about 10 μm thick adhesive layer on a polyethylene terephthalate film. An absorption spectrum of this optical filter was measured by an UV/Vis/NIR spectrophotometer V-570 manufactured by JASCO Corporation to show a λmax at 495.5 nm with a half bandwidth of 67.5 nm.

| (Composition) | |
|---|---|
| $PF_6$ salt of compound No. 1 | 2.0 mg |
| Acrylic adhesive (DB Bond 5541; manufactured by Diabond Ind, Co., Ltd.) | 20 g |
| Methyl ethyl ketone | 80 g |

Example 10

Preparation of an Optical Filter 3

The following composition was melt-blended at 260° C. for 5 minutes by a plastmil. After blending, the composition was extruded through a nozzle of 6 mm diameter and pelletized by a water cool strand pelletizer to obtain dye-containing pellets. These pellets were molded at 250° C. into a 0.25 mm thick thin plate (the content of compound No. 1, 2.0 mg/m²) using an electric press. An absorption spectrum of this thin plate was measured by an UV/Vis/NIR spectrophotometer V-570 manufactured by JASCO Corporation to show a λmax at 495.5 nm with a half bandwidth of 67.4 nm.

| (Composition) | |
|---|---|
| Iupilon S-3000 (A polycarbonate resin manufactured by Mitsubishi Gas Chemical Co., Inc.) | 100 g |
| $PF_6$ salt of compound No. 1 | 0.01 g |

Example 11

Preparation of an Optical Filter 4

An UV curable varnish of the following composition was prepared and the varnish was coated on a 188 μm thick, easy-adhesion treated polyethylene terephthalate film by a bar coater No. 9. The coated film was dried at 80° C. for 30 seconds and, thereafter irradiated with 100 mJ of UV light by a high pressure mercury lamp equipped with an infrared-cut film filter to obtain an optical filter (the content of compound No. 1, 2.0 mg/m²) having a filter layer of about 5 μm cured thickness. An absorption spectrum of this optical filter was measured by an UV/Vis/NIR spectrophotometer V-570 manufactured by JASCO Corporation to show a λmax at 495.5 nm with a half bandwidth of 67.6 nm.

| (Composition) | |
|---|---|
| ADEKA OPTOMER KRX-571-65 (An UV curable resin manufactured by Adeka Corp.; the resin content 80% by mass) | 100 g |
| $PF_6$ salt of compound No. 1 | 0.5 g |
| Methyl ethyl ketone | 60 g |

Example 12

Preparation of an Optical Filter 5

A coating liquid of the following composition was prepared and the liquid was coated on a 188 μm thick, easy-adhesion treated polyethylene terephthalate film by a bar coater No. 9. The coated film was dried at 100° C. for 3 minutes to obtain an optical filter (the content of compound No. 1, 2.0 mg/m²) with a film layer of about 10 thickness on a polyethylene terephthalate film. An absorption spectrum of this optical filter was measured by an UV/Vis/NIR spectrophotometer V-570 manufactured by JASCO Corporation to show a λmax at 495 nm with a half bandwidth of 67.3 nm.

| POLYESTER TP-220 (A polyester resin manufactured by The Nippon Synthetic Chemical Ind., Co., Ltd.) | 100 g |
|---|---|
| $PF_6$ salt of compound No. 1 | 1.0 g |
| Methyl ethyl ketone | 60 g |

Example 13

Preparation of an Optical Filter 6

Except that 2 mg of $PF_6$ salt of compound No. 3 was used instead of 2 mg of $PF_6$ salt of compound No. 1, an optical filter was prepared in the same manner as in Example 1. An absorption spectrum of the optical filter obtained was measured by an UV/Vis/NIR spectrophotometer V-570 manufactured by JASCO Corporation to show a λmax at 490.0 nm with a half bandwidth of 65.6 nm.

Example 14

Preparation of an Optical Filter 7

Except that 2 mg of $PF_6$ salt of compound No. 13 was used instead of 2 mg of $PF_6$ salt of compound No. 1, an optical filter was prepared in the same manner as in Example 1. An absorption spectrum of the optical filter obtained was measured by an UV/Vis/NIR spectrophotometer V-570 manufactured by JASCO Corporation to show a λmax at 505.0 nm with a half bandwidth of 69.2 nm.

Example 15

Preparation of an Optical Filter 8

Except that 2 mg of $PF_6$ salt of compound No. 15 was used instead of 2 mg of $PF_6$ salt of compound No. 1, an optical filter was prepared in the same manner as in Example 1. An absorption spectrum of the optical filter obtained was measured by an UV/Vis/NIR spectrophotometer V-570 manufactured by JASCO Corporation to show a λmax at 434.0 nm with a half bandwidth of 56.8 nm.

The optical filters obtained in Examples 8 to 15 using the compounds represented by the general formula (I) have sharp absorptions at specific wavelengths (between 380 and 550 nm) and it is obvious that these will exhibit excellent performances as optical filters for image display units, especially for plasma displays.

Examples 16 to 22

Manufacture of Optical Recording Materials and Optical Recording Media

The compounds obtained in Examples 1 to 7 were dissolved in 2,2,3,3-tetrafluoropropanol in a concentration of 1.0% by mass to obtain optical recording materials of Examples 16 to 22, respectively, as 2,2,3,3-tetrafluoropropanol solutions. The optical recording materials were spin coated on polycarbonate disc substrates of 12 cm diameter, which had been coated with a titanium chelate compound (T-50, manufactured by Nippon Soda Co., Ltd.), followed by hydrolysis to form a primer layer (0.01 urn). Thus, optical recording layers of 100 nm thickness were formed and optical recording media Nos. 1 to 7 of Examples 16 to 22, respectively, were obtained.

Comparative Example 1

Except that the following comparative compound No. 1 was used instead of $PF_6$ salt of compound No. 1, an optical recording material of Comparative Example 1 was prepared in the same manner as in Example 16. And an optical recording medium of comparative Example 1 was obtained using the optical recording material.

[Formula 14]

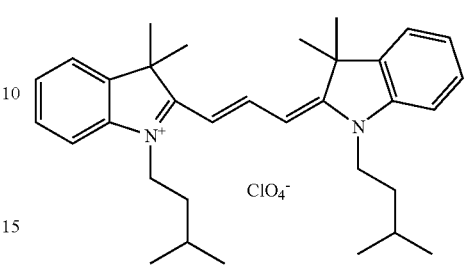

Comparative compound No. 1

Evaluation Examples 1-1 to 1-8 and Comparative Evaluation Examples 1-1 and 1-2

Evaluation of Light Resistance of the Compounds Represented by the General Formula (I)

Light resistance was evaluated of $PF_6$ salts of compounds Nos. 2 and 15, and quencher anion salts of compounds Nos. 2 and 3, each obtained in Examples 2, 5, 6, and 7, and of comparative compound 1.

First, the compounds of the present invention were dissolved in 2,2,3,3-terafluoropropanol in a concentration of 1.0% by mass to prepare 2,2,3,3-tetrafluoropropanol solutions. The solutions obtained were coated on 20 mm×20 mm polycarbonate plates by a spin coating method at 2000 rpm for 60 seconds to prepare test pieces. Evaluation was conducted by irradiating the test pieces with light of 55000 lux and, after irradiation for 24 and 48 hours, by measuring the residual rates of absorbance in the UV absorption spectra relative to the absorbance at λmax before the irradiation. It is noted that, in [Table 5], an diimmonium compound shown in [Formula 15] below was used together. The results are shown in [Table 5].

TABLE 5

|  | Compound | Diimmonium compound | Residual rate of absorbance (%) | |
|---|---|---|---|---|
|  |  |  | After 48 hrs. | After 48 hrs |
| Evaluation Example 1-1 | $PF_6$ salt of compound No. 2 | absent | 95.8 | 92.6 |
| Evaluation Example 1-2 | Quencher anion salt of compound No. 2 | absent | 94.4 | 92.6 |
| Evaluation Example 1-3 | Quencher anion salt of compound No. 3 | absent | 95.0 | 93.1 |
| Evaluation Example 1-4 | $PF_6$ salt of compound No. 2 | present | 95.7 | 87.4 |
| Evaluation Example 1-5 | Quencher anion salt of compound No. 2 | present | 96.9 | 96.2 |
| Evaluation Example 1-6 | Quencher anion salt of compound No. 3 | present | 95.7 | 94.2 |
| Evaluation Example 1-7 | $PF_6$ salt of compound No. 15 | absent | 40.5 | 23.0 |
| Evaluation Example 1-8 | $PF_6$ salt of compound No. 15 | present | 92.9 | 62.5 |
| Comparative Evaluation Example 1-1 | Comparative compound No. 1 | absent | 17.7 | 1.3 |
| Comparative Evaluation Example 1-2 | Comparative compound No. 1 | present | 81.9 | 75.3 |

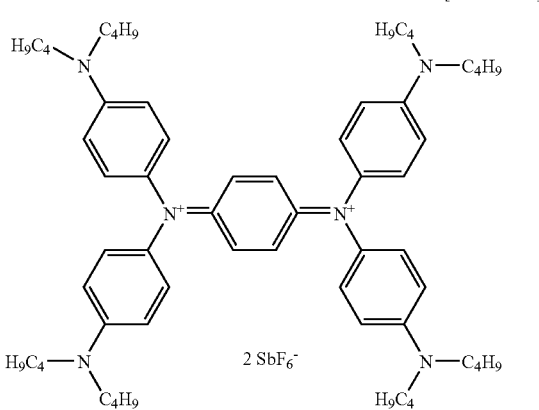

[Formula 15]

As is clear from [Table 5], the compounds of the present invention represented by the general formula (I) maintain high residual rates of absorbance even after 48 hours of light irradiation. And, also, in the case diimmonium compound was used together, no lowering of the residual rates of absorbance were observed after 48 hours of light irradiation. On the other hand, the comparative compound showed lowering of the residual rate of absorbance after 24 hours of light irradiation and, after 48 hours of irradiation, showed extensive lowering of the residual rate of absorbance. Further, when comparative compound and diimmonium compound were used together, lowering of the residual rate of absorbance was observed after both 24 and 48 hours of irradiation, showing inferior light resistance.

Evaluation Examples 2-1 to 2-5

UV absorption spectra of optical recording media Nos. 1 to 5 obtained in Examples 16 to 20 were measured, with results shown in [Table 6].

TABLE 6

|  | Optical recording medium | λmax (nm) |
| --- | --- | --- |
| Evaluation Example 2-1 | Optical recording medium No. 1 | 490.0 |
| Evaluation Example 2-2 | Optical recording medium No. 2 | 394.0 |
| Evaluation Example 2-3 | Optical recording medium No. 3 | 483.0 |
| Evaluation Example 2-4 | Optical recording medium No. 4 | *564.0, 419.0 |
| Evaluation Example 2-5 | Optical recording medium No. 5 | 516 |

*Shows an absorption (564.0 nm) due to the quencher anion.

As is clear from [Table 6], the optical recording media having optical recording layers formed by the optical recording materials of the present invention show λmax around between 380 and 550 nm in the UV absorption spectra. Thus, it was confirmed that recording by laser light of 380 to 420 nm is possible with every optical recording medium.

INDUSTRIAL APPLICABILITY

The present invention provides a novel compound having excellent absorption wavelength characteristics and light resistance suitable for optical elements. Further, the optical filter using the compound is suitable as an optical filter for image display units and an optical recording material comprising the compound is suitably used for formation of an optical recording layer of an optical recording medium.

The invention claimed is:

1. A compound represented by the following general formula (II),

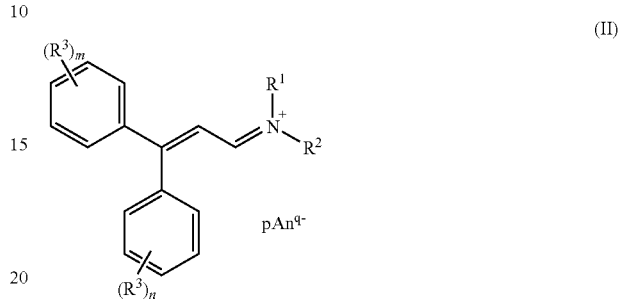

(II)

wherein;
R1 and R2 each independently represent an alkyl group having 1 to 8 carbon atoms which may be substituted;
R1 and R2 may be linked together to form a ring;
a methylene group of the alkyl group having 1 to 8 carbon atoms may be replaced by —O— or —CH=CH—;
Anq- represents a q-valent anion, where q is 1 or 2;
p represents a coefficient to keep the charge neutral;
R3 and R4 each independently represent a hydrogen atom, an alkyl group having 1 to 8 carbon atoms which may be substituted, an aryl group having 6 to 20 carbon atoms which may be substituted, an arylalkyl group having 7 to 20 carbon atoms which may be substituted, a nitro group, an amino group, a halogen atom, a cyano group, or a heterocyclic group having 2 to 20 carbon atoms;
m and n are each independently an integer from 1 to 5; and
a methylene group of the alkyl group having 1 to 8 carbon atoms may be replaced by —O— or —CH=CH—.

2. A compound represented by the following general formula (III),

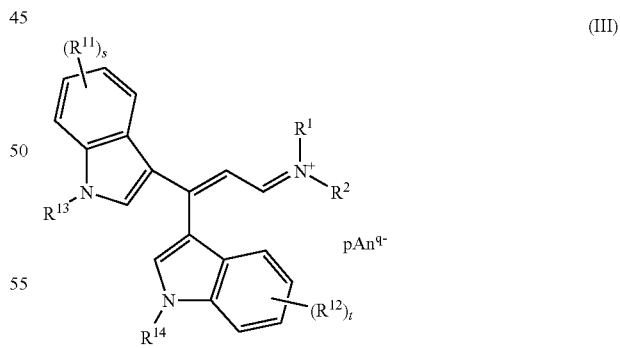

(III)

wherein
R1 and R2 each independently represent an alkyl group having 1 to 8 carbon atoms which may be substituted;
R1 and R2 may be linked together to form a ring;
a methylene group of the alkyl group having 1 to 8 carbon atoms may be replaced by —O— or —CH=CH—;
Anq- represents a q-valent anion, where q is 1 or 2;
p represents a coefficient to keep the charge neutral;

R11 and R12 each independently represent a hydrogen atom, an alkyl group having 1 to 8 carbon atoms which may be substituted, an aryl group having 6 to 20 carbon atoms which may be substituted, an arylalkyl group having 7 to 20 carbon atoms which may be substituted, a nitro group, an amino group, a halogen atom, a cyano group, or a heterocyclic group having 2 to 20 carbon atoms;

R13 and R14 each independently represent a hydrogen atom, an alkyl group having 1 to 8 carbon atoms, an aryl group having 6 to 20 carbon atoms, an arylalkyl group having 7 to 20 carbon atoms, or a substituent represented by the following general formula (IV);

s and t are each independently an integer from 1 to 5;

a methylene group of the alkyl group having 1 to 8 carbon atoms may be replaced by —O— or —CH=CH—;

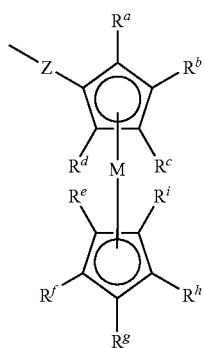

(IV)

wherein

Ra to Ri each independently represent a hydrogen atom, a hydroxyl group, or an alkyl group having 1 to 4 carbon atoms, where a methylene group of the alkyl group may be replaced by —O— or —CO—;

Z represents a direct bond or an alkylene group having 1 to 8 carbon atoms which may be substituted, where a methylene group of the alkylene group may be replaced by —O—, —S—, —CO—, —COO—, —OCO—, —SO2-, —NH—, —CONH—, —NHCO—, N=CH—, or —CH=CH—; and M represents Fe, Co, Ni, Ti, Cu, Zn, Zr, Cr, Mo, Os, Mn, Ru, Sn, Pd, Rh, Pt, or Ir.

3. An optical filter comprising at least one compound according to claim 1.

4. The optical filter according to claim 3, comprising a multiple layer structure including an adhesive layer, the adhesive layer containing the at least one compound.

5. The optical filter according to claim 3, which is for an image display unit.

6. The optical filter according to claim 5, wherein the image display unit is a plasma display.

7. An optical recording material comprising at least one compound according to claim 1.

8. An optical recording medium comprising an optical recording layer disposed on a substrate, the optical recording layer comprising the optical recording material according to claim 7.

9. An optical filter comprising at least one compound according to claim 2.

10. An optical recording material comprising at least one compound according to claim 2.

11. The optical filter according to claim 9, comprising a multiple layer structure including an adhesive layer, the adhesive layer containing the at least one compound.

12. The optical filter according to claim 11, which is for an image display unit.

13. The optical filter according to claim 12, wherein the image display unit is a plasma display.

14. An optical recording medium comprising an optical recording layer disposed on a substrate, the optical recording layer comprising the optical recording material according to claim 10.

* * * * *